(12) United States Patent
Qian

(10) Patent No.: US 7,413,344 B2
(45) Date of Patent: Aug. 19, 2008

(54) RADIOGRAPHY SYSTEM

(75) Inventor: Lei Qian, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 288 days.

(21) Appl. No.: 11/471,296

(22) Filed: Jun. 20, 2006

(65) Prior Publication Data

US 2007/0003019 A1    Jan. 4, 2007

(30) Foreign Application Priority Data

Jun. 29, 2005    (CN) .......................... 2005 1 0081848

(51) Int. Cl.
*A61B 6/08* (2006.01)
(52) U.S. Cl. ...................... 378/206; 378/147
(58) Field of Classification Search ......... 378/205–207, 378/147
See application file for complete search history.

(56) References Cited

U.S. PATENT DOCUMENTS

| | | | |
|---|---|---|---|
| 5,844,962 A * | 12/1998 | Kunert | 378/150 |
| 6,100,538 A | 8/2000 | Ogawa | |
| 6,305,842 B1 * | 10/2001 | Kunert | 378/206 |
| 6,478,462 B2 * | 11/2002 | Polkus et al. | 378/207 |
| 6,628,984 B2 | 9/2003 | Weinberg | |
| 6,739,751 B2 | 5/2004 | Williams | |
| 2003/0035508 A1 * | 2/2003 | Kasumi | 378/34 |
| 2003/0161441 A1 * | 8/2003 | Stevanovic et al. | 378/206 |
| 2005/0237517 A1 | 10/2005 | McHugh | |
| 2006/0023832 A1 | 2/2006 | Edic et al. | |

FOREIGN PATENT DOCUMENTS

JP          55-115001         9/1980

* cited by examiner

*Primary Examiner*—Hoon Song
(74) *Attorney, Agent, or Firm*—Armstrong Teasdale LLP

(57) ABSTRACT

An object of the present invention is to provide a radiography system in which an FOV in a light field agrees with an FOV in an X-ray field irrespective of a displacement of a light source. The radiography system comprises an X-ray tube, a collimator that forms an X-ray beam to be irradiated from the X-ray tube to an object of radiography, and a light source that irradiates light, which is used for ranging, to the object of radiography via the collimator. The radiography system further comprises a memory in which the magnitude of a displacement of the light source calculated in advance is stored, and a control unit that controls the opening of the collimator on the basis of the position of the light source, which is corrected based on the magnitude of a displacement read from the memory, so that an FOV of light to be used for ranging will agree with a target value.

20 Claims, 4 Drawing Sheets

RADIOGRAPHY SYSTEM

CROSS REFERENCE TO RELATED APPLICATIONS

This application claims the benefit of China Application No. 200510081848.2 filed Jun. 29, 2005.

BACKGROUND OF THE INVENTION

The present invention relates to a radiography system, or more particularly, to a radiography system that is ranged on a subject using light prior to X-irradiation.

Radiography systems are ranged on a subject using light prior to X-irradiation. After a radiography system is ranged, X-rays are irradiated. Consequently, an irradiated position to which X-rays that are an invisible radiation are irradiated can be checked in advance using a visible radiation (refer to, for example, Patent Document 1).

[Patent Document 1] Japanese Unexamined Patent Application Publication No. 55-115001 (pp. 1, FIG. 1)

In order to check a field of view (FOV) in an X-ray field in advance, light is irradiated through a collimator for X-rays. In this case, a light source must be accurately positioned with respect to a focal spot of X-rays. However, the light source may be displaced due to the effect of tolerances of components. In this case, an FOV in a light field disagrees with an FOV in an X-ray field. A radiography system cannot be ranged accurately.

SUMMARY OF THE INVENTION

An object of the present invention is to provide a radiography system in which an FOV in a light field agrees with an FOV in an X-ray field irrespective of a displacement of a light source.

In order to accomplish the above object, the present invention provides a radiography system comprising: an X-ray tube; a collimator that forms an X-ray beam to be irradiated from the X-ray tube to an object of radiography; and a light source that irradiates light, which is used for ranging, to the object of radiography via the collimator. The radiography system further comprises a memory means in which the magnitude of a displacement of the light source calculated in advance is stored, and a control means that controls the opening of the collimator on the basis of the position of the light source, which is corrected based on the magnitude of a displacement read from the memory means, so that an FOV of light to be used for ranging will agree with a target value.

Preferably, the magnitude of a displacement is the magnitude of a displacement of a ray axis in the light source, so that a light field can be agreed with an X-ray field irrespective of the displacement of the ray axis.

Preferably, the magnitude of a displacement is the magnitude of a displacement of the light source on a ray axis, so that a light field can be agreed with an X-ray field irrespective of the displacement of the light source on the ray axis.

Preferably, the magnitude of a displacement is calculated by solving an equation whose unknown is the magnitude of a displacement of a light source and whose known quantities are the other elements of the geometry of a light irradiating system and X-ray irradiating system, so that the magnitude of the displacement can be calculated correctly.

Preferably, among the known quantities, the size of the opening of the collimator is a set value, and the size of an FOV is a measured value of an FOV in a light field defined by the collimator, so that the solution can be calculated easily.

According to the present invention, a radiography system comprises an X-ray tube, a collimator that forms an X-ray beam to be irradiated from the X-ray tube to an object of radiography, and a light source that irradiates light, which is used for ranging, to the object of radiography via the collimator. The radiography system further comprises a memory means in which the magnitude of a displacement of the light source calculated in advance is stored, and a control means that controls the opening of the collimator on the basis of the position of the light source, which is corrected based on the magnitude of a displacement read from the memory means, so that an FOV of light to be used for ranging will agree with a target value. Consequently, the radiography system is realized as a modality in which an FOV in a light field will agree with an FOV in an X-ray field irrespective of a displacement of a light source.

Further objects and advantages of the present invention will be apparent from the following description of the preferred embodiments of the invention as illustrated in the accompanying drawings.

DETAILED DESCRIPTION OF THE INVENTION

Figure 1:
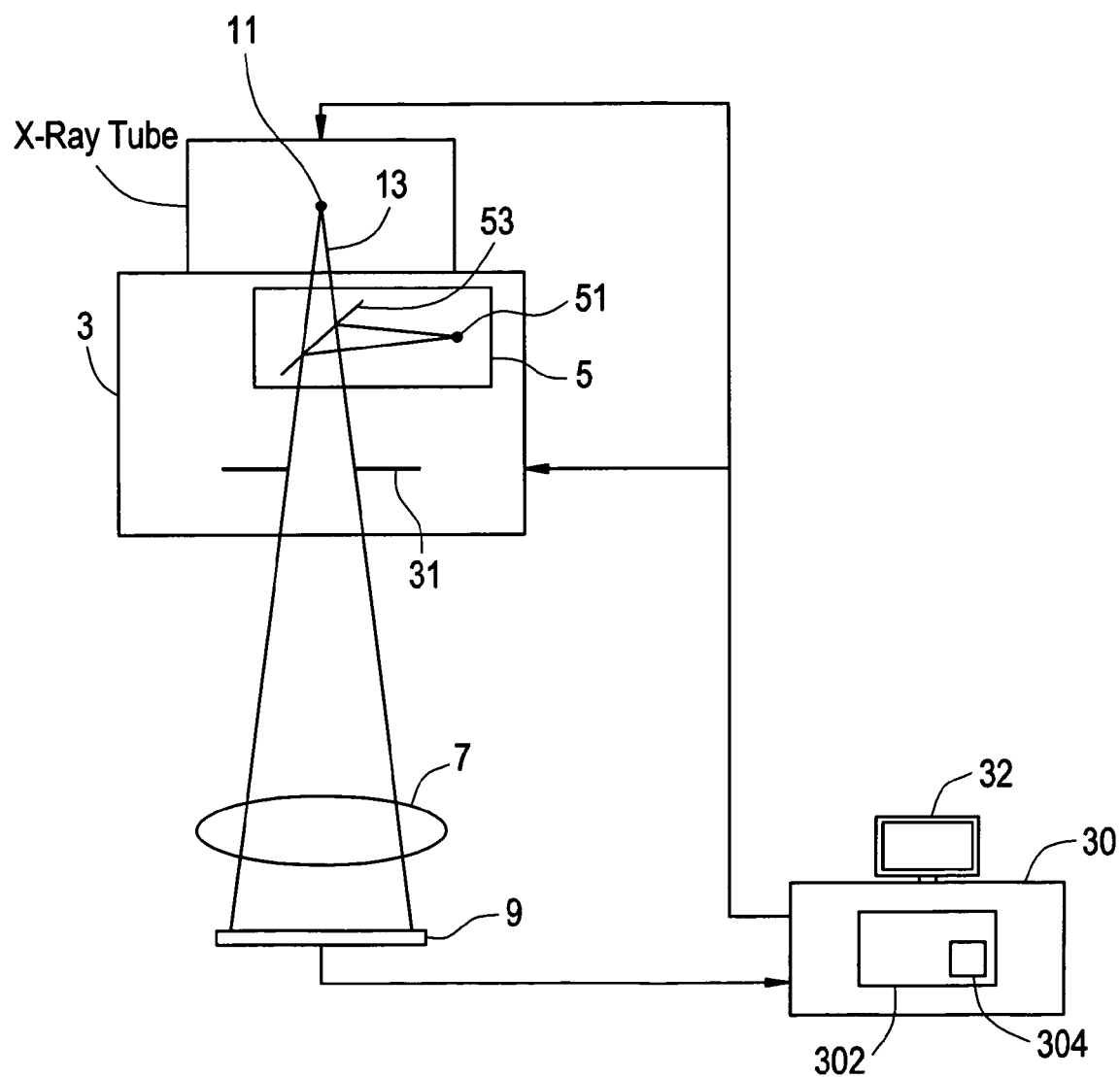
FIG. 1 shows the configuration of a radiography system that is an example of the best mode for implementing the present invention.

Referring to drawings, the best mode for implementing the present invention will be described below. Noted is that the present invention will not be limited to the best mode for implementing the present invention. FIG. 1 illustratively shows the configuration of a radiography system. The present system is an example of the best mode for implementing the present invention. The configuration of the present system is an example of the best mode for implementing the present invention in a radiography system.

As shown in FIG. 1, a radiography system is such that X-rays 13 radiated from an X-ray focal spot 11 in an X-ray tube 1 are collimated (into an X-ray beam) using a pair of blades 31 locked in a collimator box 3, and irradiated to an object of radiography 7, and that a detector 9 detects transmitted X-rays. In short, X-rays are collimated in order to define a desired field of view (FOV).

The collimator box 3 has a light irradiator 5 incorporated therein. The light irradiator 5 is interposed between the X-ray focal spot 11 and the blades 31. The light irradiator 5 includes a light source 51 and a reflecting mirror 53. The reflecting mirror 53 is inserted into the middle of a path along which the X-rays 13 propagate, whereby the direction of a visible radiation generated from the light source 51 is bent to be irradiated in the same direction as a direction in which the X-rays 13 are irradiated. Consequently, the visible radiation can be used for ranging prior to X-irradiation. Since the spacing between the blades 31 can be varied, an FOV in an X-ray field is adjustable.

A detection signal produced by the detector 9 is transferred to an operator console 30. The operator console 30 includes a computer 302. The computer 302 includes a memory 304. The operator console 30 reconstructs a fluoroscopic image of the object of radiography 7 according to an input signal, and displays the fluoroscopic image on a display 32. The detector 9 may be made of a photosensitive material that is sensitive to X-rays. In this case, the fluoroscopic image is visualized by performing development.

The operator console 30 controls the X-ray tube 1 and collimator box 3 according to operator's manipulations. As for the X-ray tube 1, the intensity of X-rays and the irradiation timing are controlled. As for the collimator box 3, the spacing between the blades 31 is controlled. An FOV in an X-ray field on a receptor surface of the detector 9 is determined with the spacing between the blades 31. An operator enters a set value of the FOV at the operator console 30.

Figure 2:
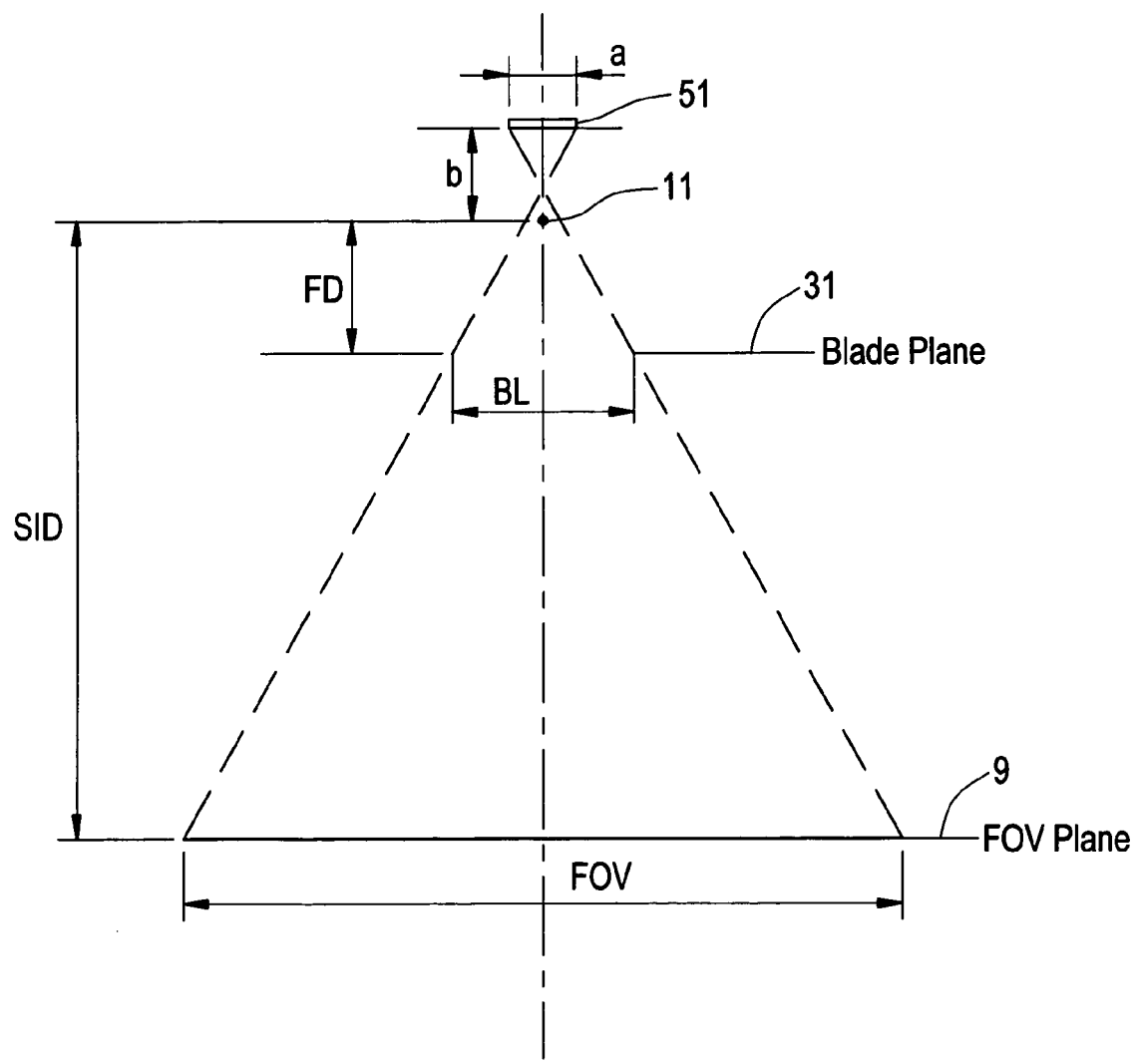
FIG. 2 shows the geometry of the radiography system that is an example of the best mode for implementing the present invention.

FIG. 2 shows the geometry of an X-ray irradiating system and a light irradiating system that are formed in the present radiography system. Incidentally, the light irradiation system is shown with a light path held unbent by the reflecting mirror. The light source 51 is a planar light source whose sides extending in a direction perpendicular to a ray axis have a length a. The X-ray focal spot 11 is a point-like focal spot whose size can be ignored. In order to form the same FOV as the one of X-rays, which are radiated from the X-ray focal spot 11, with light irradiated from the light source 51, the light source 51 is located at a distance b from the X-ray focal spot 11 in a direction opposite to a direction in which light propagates.

The distance from the X-ray focal spot 11 to the receptor surface (FOV plane) of the detector 9 is denoted by SID. The distance from the X-ray focal spot 11 to a plane containing the blades 31 (blade plane) is denoted by FD. The spacing between the blades 31 is denoted by BL. The spacing BL between the blades 31 may be referred to as a collimator opening. A field of a certain size in an X-ray field defined by the collimator opening BL is denoted by FOV.

The above elements of the geometry have a relationship given by the following formula:

$$\frac{FOV + a}{SID + b} = \frac{BL + a}{FD + b} \quad (1)$$

where FOV denotes a value arbitrarily set by an operator, BL denotes a value of the collimator opening that determines the FOV. The other elements assume fixed values. Consequently, once the FOV value is given, the opening BL of the collimator can be calculated according to the formula below.

$$BL = \frac{(FOV + a)(FD + b)}{SID + b} - a \quad (2)$$

When the FOV set value is entered, the operator console 30 uses the set value and the elements of the geometry to calculate the collimator opening BL according to the formula (2). The operator console 30 controls the blades 31 so that the spacing between the blades 31 will agree with the BL value.

Figure 3:
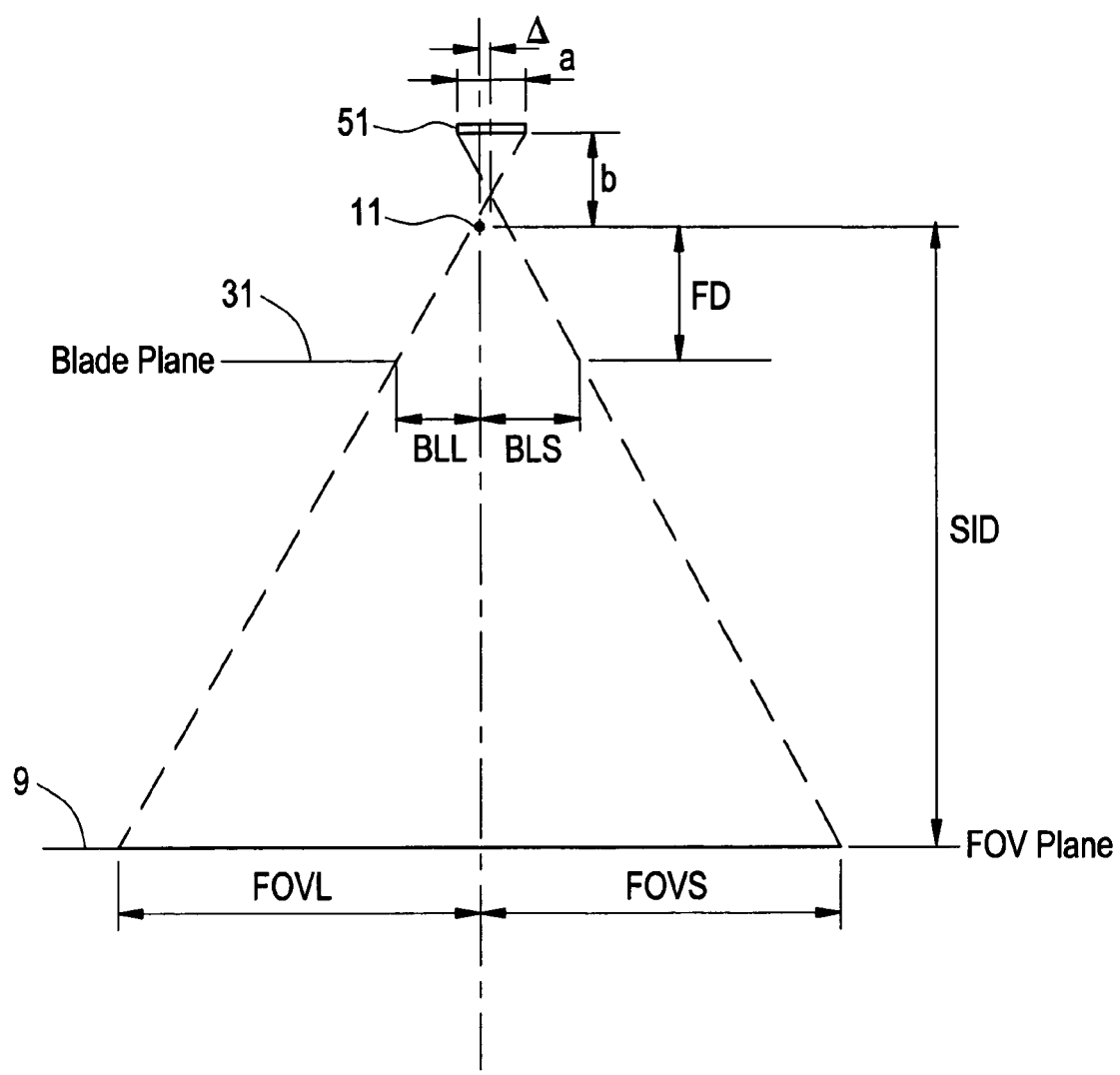
FIG. 3 shows the geometry of the radiography system that is an example of the best mode for implementing the present invention.

The position of the light source 51 may be deviated from the normal position because of the effect of tolerances of parts. FIG. 3 shows an example of a displacement of the light source 51. FIG. 3 shows a case where a ray axis in the light source 51 is deviated from the ray axis of X-rays. In this case, since the relationship expressed by the formula (1) is not established, even if the collimator opening is controlled according to the formula (2), the FOV of light disagrees with the FOV of X-rays.

In the state shown in FIG. 3, the relationships expressed below are established.

$$\frac{FOVL + a/2 + \Delta}{SID + b} = \frac{BLL + a/2 + \Delta}{FD + b} \quad (3)$$

$$\frac{FOVS + a/2 - \Delta}{SID + b} = \frac{BLS + a/2 - \Delta}{FD + b}$$

where FOVL and FOVS denote a half of an FOV defined on one side of the ray axis of X-rays and the other half thereof formed on the other side thereof. BLL and BLS denote the values of the collimator opening needed to define the FOVL and FOVS respectively. $\Delta$ denotes the magnitude of a displacement of the ray axis. The other elements assume fixed values. Consequently, the BLL and BLS values of the collimator opening determining the FOV (=FOVL+FOVS) value are given by the formulae below.

$$BLL = \frac{(FOVL + a/2 + \Delta)(FD + b)}{SID + b} - (a/2 + \Delta) \quad (4)$$

$$BLS = \frac{(FOVS + a/2 - \Delta)(FD + b)}{SID + b} - (a/2 - \Delta)$$

In the formulae (4), since the magnitude of a displacement of the ray axis, $\Delta$, is an unknown, if the magnitude of a displacement $\Delta$ remains unknown, the collimator opening cannot be calculated. The magnitude of a displacement of the ray axis, $\Delta$, is therefore specified as described below. First, the collimator opening is controlled so that the BLL and BLS values will be equal to each other. In this state, the FOVL and FOVS values are actually measured and a difference between them is calculated. The difference between the FOVL and FOVS values is given by the formula below.

$$FOVL - FOVS = \frac{2\Delta(SID + b) + (BLL - BLS)(SID + b)}{FD + b} - 2\Delta \quad (5)$$

$$= \frac{2\Delta(SID + b)}{FD + b} - 2\Delta$$

The formula (5) is an equation whose unknown is the magnitude of a displacement, $\Delta$, alone. By solving the equation, the magnitude of a displacement of the ray axis, $\Delta$, is worked out as follows:

$$\Delta = \frac{(FOVL - FOVS)(FD + b)}{2(SID - FD)} \quad (6)$$

The above calculation is performed by a computer 302. The magnitude of a displacement of the ray axis is calculated by solving an equation whose unknown is the magnitude of a displacement of the ray axis and whose known quantities are the other elements of the geometry of a light irradiating system and X-ray irradiating system. Therefore, the magnitude of a displacement can be calculated correctly. Moreover, among the known quantities, the size of the collimator opening is a set value, and the size of an FOV is a measured value of the FOV in a light field defined by the collimator. Therefore, the solution of the equation can be worked out easily.

The result of the calculation is stored in the memory 304 as one of the elements of the geometry. The value of the magnitude of a displacement of the ray axis, Δ, is specified at the time of, for example, installing the radiography system at an operation site or during maintenance performed periodically or at any time.

When the radiography system is in operation, the thus specified value of the magnitude of a displacement of the ray axis, Δ, is used to calculate the BLL and BLS values of the collimator opening associated with the set values FOVL and FOVS of the FOV. The collimator opening is controlled based on the calculated values, whereby the FOV in a light field is agreed with the FOV in an X-ray field irrespective of a displacement of a ray axis. A set value of the FOV is given as the sum of the FOVL and FOVS values, and the FOVL and FOVS values are equal to each other.

Figure 4:
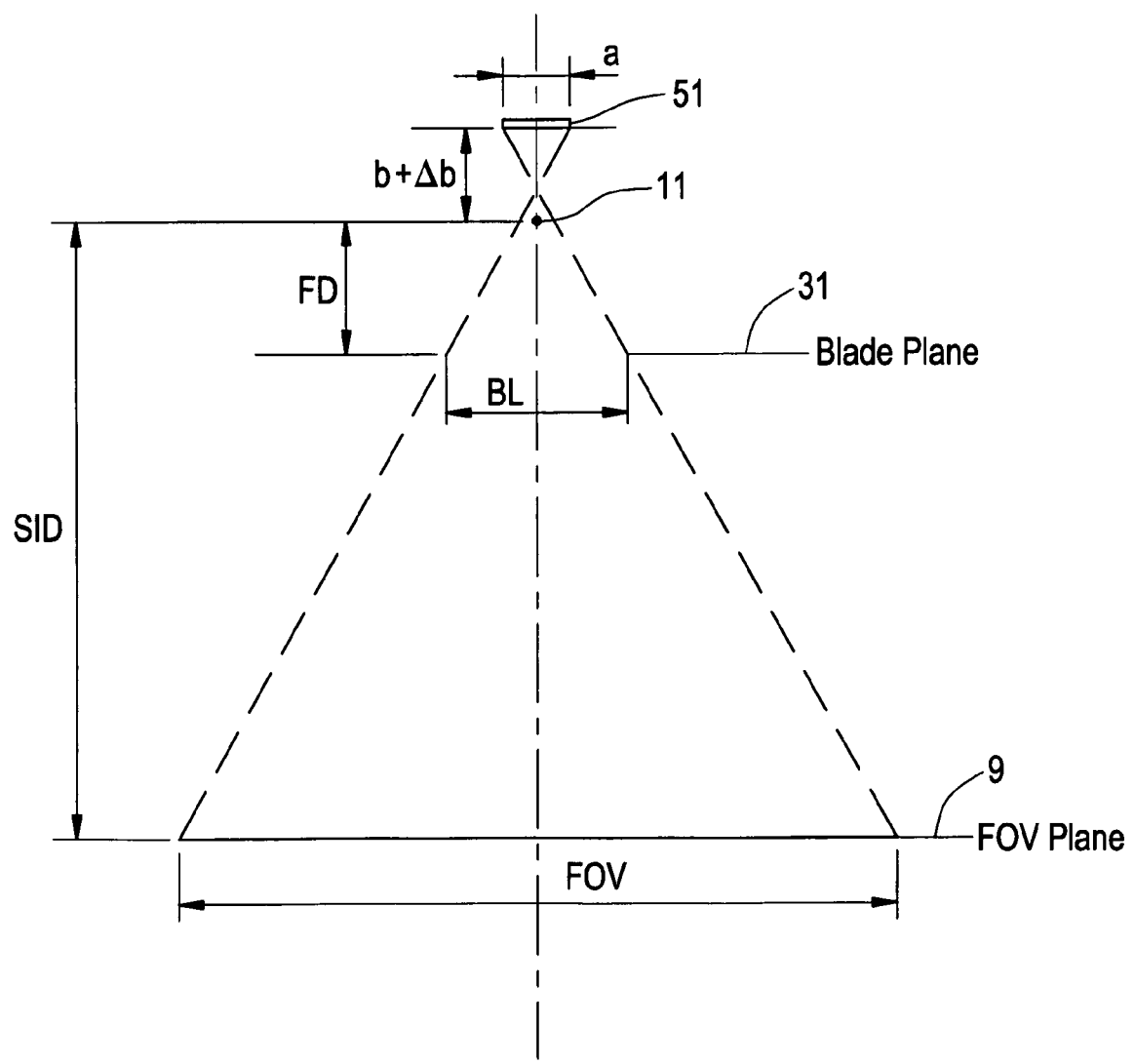
FIG. 4 shows the geometry of the radiography system that is an example of the best mode for implementing the present invention.

FIG. 4 shows another example of a displacement of the light source 51. FIG. 4 shows a case where the light source 51 is displaced on a ray axis. The magnitude of the displacement is denoted by Δb. In this state, the relationship expressed by the formula (1) is not established. Therefore, even if the collimator opening is controlled according to the formula (2), the FOV of light disagrees with the FOV of X-rays.

In the state shown in FIG. 4, the relationship expressed by the formula below is established.

$$\frac{FOV + a}{SID + b + \Delta b} = \frac{BL + a}{FD + b + \Delta b} \quad (7)$$

where Δb denotes the magnitude of a displacement of the light source, and the other elements assume fixed values. Consequently, the collimator opening BL associated with the FOV is given by the following formula:

$$BL = \frac{(FOVL + a)(FD + b + \Delta b)}{SID + b + \Delta b} - a \quad (8)$$

In the formula (8), the magnitude of a displacement of the light source, Δb, is an unknown. As long as the Δb remains unknown, the collimator opening cannot be calculated. Therefore, the magnitude of a displacement of the light source, Δb, is specified as described below. First, an ideal value FOVi of the FOV is determined, and the value of the collimator opening BL associated with the value FOVi is calculated according to the formula (2). Namely, $$BL = \frac{(FOVi + a)(FD + b)}{SID + b} - a \quad (9)$$

The collimator opening is then controlled so that the size thereof will be equal to the value BL. In this state, the size of an FOV is measured in order to obtain an actually measured value FOVa. The value FOVa is affected by the magnitude of a displacement of the light source, Δb, and expressed by the formula below.

$$FOVa = \frac{(SID + b + \Delta b)(BL + a)}{FD + b + \Delta b} - a \quad (10)$$

The formula (10) is an equation whose unknown is the magnitude of a displacement Δb alone. By solving the equation, the magnitude of a displacement of the light source, Δb, is calculated as follows:

$$\Delta b = \frac{SID(BL + a) - FD(FOVa + a)}{FOVa - BL} - b \quad (11)$$

This calculation is performed by the computer 302. Since the magnitude of a displacement of the light source is calculated by solving an equation whose unknown is the magnitude of a displacement of the light source and whose known quantities are the other elements of the geometry of a light irradiating system and X-ray irradiating system. Therefore, the magnitude of a displacement can be calculated accurately. Moreover, among the known quantities, the size of the collimator opening is a set value, and the size of an FOV is a measured value of the FOV in a light field defined by the collimator. The solution can be calculated easily.

The result of the calculation is stored in the memory 304 as one of the elements of the geometry. The value of the magnitude of a displacement of the light source, Δb, is specified at the time of, for example, installing the radiography system at an operation site or during maintenance performed regularly or at any time.

When the radiography system is in operation, the thus specified value of the magnitude of a displacement of the light source, Δb, is used to calculate the value of the collimator opening BL associated with a set value of an FOV according to the formula (8). The collimator opening is controlled based on the calculated value. Consequently, an FOV in a light field can be agreed with an FOV in an X-ray field irrespective of a displacement of the light source.

Many widely different embodiments of the invention may be configured without departing from the spirit and the scope of the present invention. If should be understood that the present invention is not limited to the specific embodiments described in the specification, except as defined in the appended claims.

The invention claimed is:

1. A radiography system having an X-ray tube, a collimator that forms an X-ray beam to be irradiated from the X-ray tube to an object of radiography, and a light source that irradiates light, which is used for ranging, to the object of radiography via the collimator, comprising:
    a memory device in which the magnitude of a displacement of the light source calculated in advance is stored; and
    a control device that controls the opening of the collimator on the basis of the position of the light source, which is corrected based on the magnitude of a displacement read from the memory device, so that an FOV of light to be used for ranging will agree with a target value.

2. The radiography system according to claim 1, wherein the magnitude of a displacement is the magnitude of a displacement of a ray axis in the light source.

3. The radiography system according to claim 1, wherein the magnitude of a displacement is the magnitude of a displacement of the light source on a ray axis.

4. The radiography system according to claim 1, wherein the magnitude of a displacement is calculated by solving an equation whose unknown is the magnitude of a displacement of the light source and whose known quantities are the other elements of the geometry of a light irradiating system and X-ray irradiating system.

5. The radiography system according to claim 4, wherein among the known quantities, the size of the opening of the collimator is a set value, and the size of an FOV is a measured value of the FOV in a light field defined by the collimator.

6. A method for programming a radiography system that includes a light source, a radiation source, and a collimator, said method comprising:

calculating a magnitude of displacement between the light source and the radiation source;

storing the calculated magnitude of displacement into a computer;

programming the computer to control an opening of the collimator based on the calculated magnitude of displacement.

7. A method in accordance with claim 6, further comprising programming calculating a magnitude of displacement such that a field of view of the light source is approximately equal to a field of view of the radiation source.

8. A method in accordance with claim 6, wherein calculating a magnitude of displacement further comprises:

defining a field of view of the radiation source;

determining a field of view of the light source; and calculating the magnitude of displacement between the field of view of the light source and the field of view of the radiation source.

9. A method in accordance with claim 8 further comprising calculating the magnitude of displacement in accordance with $$\frac{FOVL + a/2 + \Delta}{SID + b} = \frac{BLL + a/2 + \Delta}{FD + b}$$

$$\frac{FOVS + a/2 - \Delta}{SID + b} = \frac{BLS + a/2 - \Delta}{FD + b}$$

where

FOVL is equal to ½ FOV defined on a first side of the X-ray radiation source;

FOVL is equal to ½ FOV defined on a second side of the X-ray radiation source;

SID is the distance from an x-ray focal spot to a detector surface;

BLL and BLS are equal to collimator opening;

FD is distance between the x-ray focal spot and a collimator plane;

Δ is the displacement between the field of view of the light source and the field of view of the radiation source;

a is the width of the light source; and b is the distance from the light source to a radiation source focal point.

10. A method in accordance with claim 9 further comprising calculating BLL and BLS in accordance with $$BLL = \frac{(FOVL + a/2 + \Delta)(FD + b)}{SID + b} - (a/2 + \Delta)$$

$$BLS = \frac{(FOVS + a/2 - \Delta)(FD + b)}{SID + b} - (a/2 - \Delta).$$

11. A method in accordance with claim 10 further comprising calculating a difference between FOVL and FOVS in accordance with $$FOVL - FOVS = \frac{2\Delta(SID + b) + (BLL - BLS)(SID + b)}{FD + b} - 2\Delta$$

$$= \frac{2\Delta(SID + b)}{FD + b} - 2\Delta.$$

12. A method in accordance with claim 11 further comprising the magnitude of displacement in accordance with $$\Delta = \frac{(FOVL - FOVS)(FD + b)}{2(SID - FD)}.$$

13. A method in accordance with claim 8 further comprising the magnitude of displacement in accordance with $$\frac{FOV + a}{SID + b + \Delta b} = \frac{BL + a}{FD + b + \Delta b}$$

where

FOV is a predetermined field of view of the radiation source;

a is the width of the light source; and b is the distance from the light source to the x-ray focal point, SID is the distance from an x-ray focal spot to a detector surface;

FD is distance between the x-ray focal spot and a collimator plane;

BL is the width of a collimator opening; and

Δb is the magnitude of displacement of the light source with respect to the radiation source.

14. A method in accordance with claim 13 further comprising calculating the width of the collimator opening BL in accordance with $$BL = \frac{(FOVL + a)(FD + b + \Delta b)}{SID + b + \Delta b} - a.$$

15. A method in accordance with claim 14 further comprising calculating an actual field of view (FOVa) of the radiation source in accordance with $$FOVa = \frac{(SID + b + \Delta b)(BL + a)}{FD + b + \Delta b} - a.$$

16. A method in accordance with claim 15 further comprising calculating an actual magnitude of displacement Δb in accordance with $$\Delta b = \frac{SID(BL + a) - FD(FOVa + a)}{FOVa - BL} - b.$$

17. A method in accordance with claim 16 repositioning the light source by a distance Δb such the light source field of view is substantially aligned with the radiation source field of view.

18. A radiography system comprising:

an X-ray tube;

a collimator that forms an X-ray beam to be irradiated from said X-ray tube to an object of radiography;

a light source that irradiates light, which is used for ranging, to the object of radiography via said collimator; and a control device coupled to said x-ray tube and said collimator, said control device is configured to determine a magnitude of a displacement between said light source and said x-ray source and control an opening of said collimator such that a field of view of said light source is substantially similar to a field of view target value.

19. A radiography system in accordance with claim 18 wherein to determine the magnitude of displacement said control device is further configured to determine the magnitude of a displacement of a ray axis in the light source.

20. A radiography system in accordance with claim 18 wherein to determine the magnitude of displacement said control device is further configured to solve an equation whose unknown is the magnitude of a displacement of said light source and whose known quantities are the other elements of the geometry of a light irradiating system and X-ray irradiating system.

* * * * *